United States Patent [19]
Goto et al.

[11] Patent Number: 5,652,198
[45] Date of Patent: Jul. 29, 1997

[54] HERBICIDALLY ACTIVE TETRAZOLINONES

[75] Inventors: Toshio Goto, Shimotsuga-gun; Seishi Ito, Oyama; Yukiyoshi Watanabe, Saitama; Shin-ichi Narabu, Ibaraki; Akihiko Yanagi, Tochigi, all of Japan

[73] Assignee: Nihon Bayer Agrochem K.K., Tokyo, Japan

[21] Appl. No.: 611,580

[22] Filed: Mar. 6, 1996

[30] Foreign Application Priority Data

Mar. 10, 1995 [JP] Japan .................. 7-079310

[51] Int. Cl.⁶ .................. C07D 257/04
[52] U.S. Cl. .................. 504/261; 548/251
[58] Field of Search .................. 548/251; 504/261

[56] References Cited

U.S. PATENT DOCUMENTS

| | | |
|---|---|---|
| 4,618,365 | 10/1986 | Covey et al. . |
| 4,826,529 | 5/1989 | Covey et al. . |
| 4,830,661 | 5/1989 | Covey et al. . |
| 4,956,469 | 9/1990 | Covey et al. . |
| 5,003,075 | 3/1991 | Covey et al. . |
| 5,019,152 | 5/1991 | Covey et al. . |
| 5,120,346 | 6/1992 | Covey et al. . |
| 5,342,954 | 8/1994 | Goto et al. . |
| 5,344,814 | 9/1994 | Goto et al. . |
| 5,347,009 | 9/1994 | Goto et al. . |
| 5,347,010 | 9/1994 | Goto et al. . |
| 5,362,704 | 11/1994 | Goto et al. . |

FOREIGN PATENT DOCUMENTS

| | | |
|---|---|---|
| 146279 | 6/1985 | European Pat. Off. . |
| 0612735 | 8/1994 | European Pat. Off. . |
| 0646577 | 4/1995 | European Pat. Off. . |
| 0672663 | 9/1995 | European Pat. Off. . |

*Primary Examiner*—Jacqueline Haley
*Attorney, Agent, or Firm*—Sprung Horn Kramer & Woods

[57] ABSTRACT

Selective herbicidal tetrazolinones of the formula

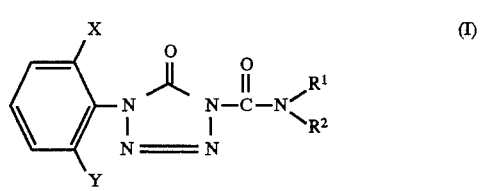

(I)

wherein

X is hydrogen or halogen,

Y is hydrogen or $C_{1-4}$ alkyl, $R^1$ is $C_{1-4}$ alkyl, and $R^2$ is cycloheptyl or cyclooctyl.
and synergistic mixtures thereof.

10 Claims, No Drawings

HERBICIDALLY ACTIVE TETRAZOLINONES

The present invention relates to novel tetrazolinones and use thereof as herbicides for paddy field cultivation.

It has been already known that certain tetrazolinone derivatives exhibit herbicidal activities (see: Japanese Patent Kokai Publications Sho 62-12767 and 60-146879; U.S. Pat. Nos. 4,956,469, 5,019,152 and 5,003,075).

There have now been found novel tetrazolinones of the formula (I)

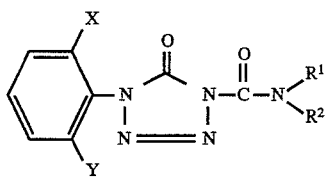

wherein

X is hydrogen or halogen,

Y is hydrogen or $C_{1-4}$ alkyl, $R^1$ is $C_{1-4}$ alkyl, and $R^2$ is cycloheptyl or cyclooctyl.

The compounds of formula (I) according to the invention can be produced, for example, by reacting a compound of the formula

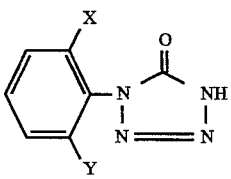

with a compound of the formula:

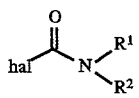

wherein hal is a leaving group such as chlorine, bromine, or the like.

Surprisingly, the tetrazolinones of formula (I) according to the invention exhibit herbicidal activity much superior to that of the known compounds described in Japanese Patent Kokai Publications Sho 62-12767 and 60-146879. U.S. Pat. Nos. 4,956,469, 5,019,152 and 5,003,075, and particularly they are selectively active against paddy field weeds but not against paddy rice plants.

Those compounds of formula (I) are preferred wherein

X is chlorine,

Y is hydrogen or methyl, $R^1$ is ethyl or m-propyl, and $R^2$ is cycloheptyl or cyclooctyl.

The foregoing process of preparation is illustrated by the following reaction scheme, utilizing 1-(2-chlorophenyl)-5 (4H)-tetrazolinone and N-cycloheptyl-N-ethylcarbamoyl chloride as starting materials:

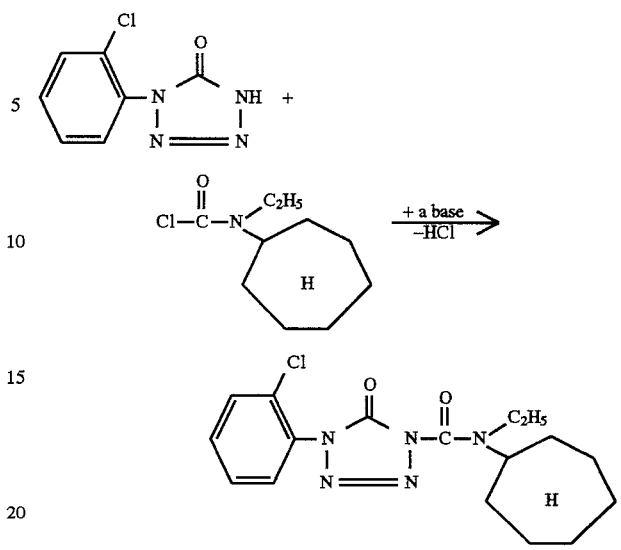

The starting materials of formula (II) can be synthesized by a method similar to that described in The Journal of Organic Chemistry, Vol. 45, No. 21, 5130–5136 (1980) or The Journal of American Chemical Society, Vol. 81, 3076–3079 (1959). Representative examples of the compounds of formula (II) include the following compounds:
1-(2-chlorophenyl)-5(4H)-tetrazolinone.
1-(2-chloro-6-methylphenyl)-5(4H)-tetrazolinone, and
1-phenyl-5(4H)-tetrazolinone.

The starting materials of the formula (III) are well known in the field of organic chemistry, and specific examples thereof include the following compounds:
N-cycloheptyl-N-ethylcarbamoyl chloride,
N-cycloheptyl-N-n-propylcarbamoyl chloride, and
N-cyclooctyl-N-ethylcarbamoyl chloride.

The reaction of the compound (II) with the compound (III) can be carried out in an appropriate diluent such as an inert organic solvent. Examples of useful diluents include aliphatic, alicyclic and aromatic hydrocarbons (which may optionally be chlorinated), such as pentane, hexane, cyclohexane, petroleum ether, ligroin, benzene, toluene, xylene, dichloromethane, chloroform, carbon tetrachloride, chlorobenzene and dichlorobenzene; ethers such as diethyl ether, methyl ethyl ether, di-isopropyl ether, dibutyl ether, dioxane, dimethoxyethane (DME), tetrahydrofuran (THF) and diethyleneglycol dimethyl ether (DGM); nitriles such as acetonitrile and propionitrile; acid amides such as dimethylformamide (DMF), dimethylacetamide (DMA), N-methylpyrrolidone, 1,3-dimethyl-2-imidazolidinone and hexamethylphosphoric triamide (HMPA); sulfones and sulfoxides such as dimethylsulfoxide (DMSO) and sulfolane; bases such as pyridine; and others.

The process can be carried out in the presence of acid binding agents, e.g. inorganic bases such as carbonates and bicarbonates of alkali metals including sodium hydrogen carbonate, patassium hydrogen carbonate, sodium, carbonate, potassium carbonate and the like; and organic bases such as tertiary amines, dialkylaminoanilines and pyridines including triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo [2,2,2] octane (DABCO), 1,8-diazabicyclo [5,4,0] undec-7-ene (DBU), and the like.

Furthermore, in the reaction, 4-dimethylamino-pyridine can be used as a catalyst and/or the add binding agent in order selectively to synthesize the desired compound.

The reaction can be conducted over a broad range of temperatures but it is preferable to carry it out generally in the temperature range of about −30° to about 200° C., preferably about −20° to about 130° C. The reaction should preferably be conducted under atmospheric pressure but may also be carried out under elevated or reduced pressure.

In carrying out the process, the desired compound of the formula (I) can be obtained by reacting 1 mole of the compound of formula (II), in a diluent such as toluene, with 1 to 1.2 moles of the compound of formula (III), in the presence of 1 to 1.2 moles of the acid-binding agent and 4-dimethylaminopyridine.

As is clear from the Biological Test Examples hereinbelow, the compounds according to the invention exhibit excellent herbcidal activities against paddy field weeds and little or no phytototxicity to rice plants.

Further, it has been found that herbicidal compositions having particularly high herbicidal activities are obtained when the compounds according to the invention are used in combination with at least one other herbicidal compound selected from the group consisting of herbicidal sulfamides, herbicidal pyrazoles, herbicidal propionanilides, herbicidal triazines, herbicidal carbamates, herbicidal diphenyl ethers, herbicidal pyrimidines and herbicidal acid amides.

Surprisingly, the foregoing mixture of herbicides according to the present invention have been found to exhibit herbicidal effects substantially higher than the sum of the herbicidal effects exhibited individually by the herbicidally active, respective components and, as a result, the concentration of each of the active compounds can be substantially reduced when practicing weed control operations, while at the same time, a wide herbicidal spectrum can be obtained. Further, the herbicidal compositions according to the present invention have been found to expand the period of possible application, for example, in paddy rice cultivation, and exhibit excellent herbicidal activities over a period from the early stage of weed-emergence to the weed-growing, with prolonged duration of activity and excellent residual effect, as well as phytotoxicity-free, excellent herbicial effect on rice plants.

In the above herbicidal compositions, specific examples of the herbicidal compounds which can be used in combination with the compounds of formula (I) according to the invention are as follows:

herbicidal sulfonamides:
N-2-biphenylylsulfonyl N'-(4,6-dimethoxy-1,3,5-triazin-2-yl)urea
ethyl 5-[3-(4,6-dimethoxypyrimidin-2-yl)ureido-sulfonyl]-1-methylpyrazol -4-carboxylate,
methyl 2-[3-(4,6- dimethoxypyrimidin-2-yl)ureido-sulfonyl-methyl]benzoate,
3-(4,6-dimethoxy-1,3,5-triazin-2-yl)-1-[2-(2-methoxyethoxy)-phenylsulfonyl]urea,
N-(2-chloroimidazol[1,2-a]pyridin-3-yl-sulfonyl)-N'-(4,6-dimethoxy-2-pyrimidinyl)urea,
N'-(4,6-dimethoxypyrimidin-2-yl)-N''-(4-methylphenyl-sulfonyl-amino)-N'''-(4-ethoxycarbonyl-1-methylpyrazol- 5-yl-sulfonyl) guanidine,
N-(2-cyclopropylcarbonylphenylsulfamoyl)-N'-(4,6-dimethoxy-pyrimidin-2-yl)urea, etc.

These compounds are well known and described in Japanese Patent Kokoku Publication Sho 59-481; Japanese Patent Kokai Publications Sho 57-1 12379, Sho 57-56452, Sho 59-122488, Hei 1-38091 , Hei 1-70475 etc.

herbicidal pyrazoles:
4-(2,4- dichlorobenzoyl)-1,3-dimethylpyrazol-5-yl p-toluenesulfonate,
2-[4-(2,4-dichlorobenzoyl)-1,3-dimethylpyrazol-5-yl] acetophenone,
2-[4-(2,4-dichloro-m-tolyl)-1,3-dimethylpyrazol-5-yloxy]-4-methylacetophenone, etc.

herbicidal propionanilides:
2-(β-naphthyloxy)propionanilide,
(RS)-2-(2,4-dichloro-m-tolyloxy)propionanilide, etc.

herbicidal triazines:
2,4-bis(ethylamino)-6-(methylamino)-1,3,5-triazine,
2-ethylamino-4-(1,2-dimethylpropylamino)-6-methylthio-1,3,5-triazine, etc.

herbicidal carbamates:
S-p-chlorobenzyl diethylthiocarbamate,
S-1-methyl-1-phenylethyl piperidin-1-carbothioate,
S-benzyl 1,2-dimethylpropyl(ethyl)thiocarbamate, etc.

herbicidal diphenyl ethers:
2,4,6-trichlorophenyl-4'-nitrophenyl ether,
2,4-dichlorophenyl-3'-methoxy-4'-nitrophenyl ether, etc.

herbicidal acid amides:
(RS)-2-bromo-N-(α,α-dimethylbenzyl)-3,3-dimethylbutyramide, etc.

herbicidal pyrimidines:
methyl 2-[(4,6-dimethoxy-2-pyrimidinyl)oxy]-6-[1-(methoxyimino)ethyl]-benzoate, etc.

The above herbicidal compounds are described, for example, in Pesticide Manual, 1991, published by The British Crop Protect Council.

Further, the above herbicidal pyrimidines are described in BCPC Weeds, 1993, Brighton, Nov. 22–25th, 1993, Vol. 1., Ref. 2-b.

In the herbicidal mixtures according to the invention, the mixed weight ratio of each effective component can be varied over a relatively wide range, but generally per part by weight of the compound of the formula (I), there are employed per part by weight of the compound of formula (I)

0.01–2 parts by weight, preferably 0.05–1 part by weight, of the herbicidal sulfonamides, 2.5–35 parts by weight, preferably 3–15 parts by weight, of the herbicidal pyrazoles, 0.6–50 parts by weight, preferably 2.0–28 parts by weight, of the herbicidal propionanilides, 0.06–10 parts by weight, preferably 0.15–6 parts by weight, of the herbicidal triazines, 3–15 parts by weight, preferably 5–10 parts by weight, of the herbicidal carbamates, 5–35 parts by weight, preferably 7–15 parts by weight, of the herbicidal diphenyl ethers, 3.5–25 parts by weight, preferably 4.0–10 parts by weight, of the herbicidal acid amides, and 0.01–2 parts by weight, preferably 0.1–1 part by weight, of the herbicidal pyrimidines.

The herbicidal compositions according to the invention exhibit strong herbicidal activity against various weeds, for example, of the following species:

Dicotyledon weeds of the genera:
Polygonum, Rorippa, Rotala, Lindernia, Bidens, Dopatrium, Eclipta, Elatine, Gratiola, Vandellia, Ludwigia, Oenanthe, Ranunculus, Deinostema, etc.

Monocotyledon weeds of the genera:
Echinochloa, Panicum, Poa, Cyperus, Monochoria, Fimbristylis, Sagittaria, Eleocharis, Scirpus, Alisma, Aneilema, Blyxa, Eriocaulon, Potamogeton, etc.

More specifically, they can be used to control paddy field weeds, for example, of the following species:
scientific name (plant name)
Dicotyledon weeds:
*Rotala indica* Koehne (Indian toothcup)

Lindernia Procumbens Philcox (common falsepimpernel)
*Ludwigia prostrata* Roxburgh (false loosestrife)
*Potamogeton distinctus* A. Benn (bog pondweed)
*Elatine triandra* Schk (long stemmed water wort)
*Oenanthe javanica* (Blume) DC. (dropwort)
Monocotyledon weeds:
*Echinochloa oryzicola* Vasing (barnyardgrass)
*Monochoria vaginalis* Presl (monochoria)
*Eleocharis acicularis* L. (cow hairs)
Eleocharis Kuroguwai Ohwi (water chestnut)
*Cyperus difformis* L. (smallflower)
*Cyperus serotinus* Rottboel (water nutgrass)
*Sagittaria pygmaea* Miq (Japanese ribbon wapato)
*Alisma canaliculatum* (narrow-leaved arrowhead)
A. Br. et Bouche
*Scirpus juncoides* Roxburgh (bulrush).

However, the uses of the compounds and herbicidal compositions according to the inventions are in no way restricted to the above genera, but also extend in the same manner, to other paddy field weeds.

The compounds and herbicidal compositions according to the inventions can be converted into any form of conventional formulations.

Such formulations are exemplified, by solutions, emulsions, wettable powders, suspensions, powders, soluble powders, granules, tablets, suspension-emulsion concentrates, microcapsules in polymeric substances, jumbo agents, etc.

These formulations can be prepared by any of the methods known per se and they can be produced for instance, by mixing the active compound with extenders, that is liquid diluents and/or solid carriers, optionally with the use of surface-active agents, that is emulsifying agents and/or dispersing agents and/or foam-forming agents.

Liquid diluents are exemplified by aromatic hydrocarbons (e.g., xylene, toluene, alkylnaphthalene, etc.), chlorinated aromatic or chlorinated aliphatic hydrocarbons (e.g. , chlorobenzene, ethylene chloride,. methylene chloride, etc.), aliphatic hydrocarbons [e.g. , cyclohexane, paraffins (such as petroleum fractions, mineral and vegetable oils), etc.], alcohols (e.g., butanol, glycols, and ethers and esters thereof, etc.), ketones (e.g., acetone, methyl ethyl ketone, methyl isobutyl ketone, cyclohexanone, etc.), highly polar solvents (e.g., dimethylformamide, dimethylsulfoxide, etc.), water and others. In the case of using water as the extender, an organic solvent can be used optionally as an auxiliary solvent.

The solid carriers are exemplified by ammonium salts and natural soil minerals (such as kaolin, clay, talc, chalk, quarts, attapulgite, montmorillonite, diatomaceous earth, etc.) and synthetic soil minerals (such as highly-disperse silicic acid, alumina, silicate salts, etc.). The solid carriers for granules are exemplified by ground and classified rocks (such as calcite, marble, pumice, sepiolite, dolomite, etc.), synthetic granules of inorganic or organic meals and granules of organic materials such as sawdust, coconut shells, corn and tobacco stalks.

As emulsifying agents and/or foam-forming agents there are suitable for example, non-ionic and anionic emulsifiers, such as polyoxyethylene-fatty acid esters and polyoxyethylene fatty alcohol ethers (for example alkylaryl polyglycol ethers, alkyl sulfonates, alkyl sulfates, aryl sulfonates) as well as albumin hydrolysis products.

As dispersing agents there are suitable, for example, lignin sulfite waste liquors and methylcellulose.

Adhesives may also be used optionally in formulations (such as powders, granules, jumbo agents, emulsions) and such adhesives are exemplified by carboxymethylcellulose, natural and synthetic polymers (e.g., gum arabic, polyvinyl alcohol, polyvinyl acetate, etc.), natural phospholipids (e.g., cephalins and lecithins) and synthetic phospholipids. As further additives, mineral and vegetable oils can be incorporated.

It is also possible to use colorants such as inorganic pigments, for example iron oxide, titanium oxide, and Prussian Blue, and organic dyestuffs, such as alizarin dyestuffs, azo dyestuffs and metal phthalocyanine dyestuffs, and trace nutrients such as salts, for example iron, magnesium, boron, copper, molybdenum and zinc.

The formulations in general contain between 0.1 and 95% by weight, preferably between 0.5 and 90% by weight, of the active compound.

The herbicides and the active compounds in the herbicidal compositions according to the invention can be used for controlling undesired weeds as they are or in the form of such formulations. The formulations may be either prepared, in advance in the form of a final formulation or prepared by tank-mixing immediately before use. Further, the herbicides and the herbicidal compositions according to the invention may contain other known active compounds. For instance, those which can be usually used in paddy field cultivation such as a fungicide, bactericide, insecticide, plant growth regulator, plant nutrition agent, soil improvement agent, phytotoxicity mitigating agent, still other herbicide, etc. Preferred examples are: 1–200 parts by weight, preferably 2–100 parts by weight, of 1-(α,α-dimethylbenzyl)-3-p-tolylurea as a phytotoxicity mitigating agent per part by weight of the above herbicidal compound, or a herbicidal sulfonamide can be added to the herbicidal compositions according to the invention.

The active compounds can be used directly as they are, in a form of a formulation thereof, or in a use form prepared from such a formulation by further dilution, such as ready-to-use solutions, emulsions, suspensions, powders, wet table powders, granules, etc. They can be applied by any of conventional methods such as liquid watering, spraying, atomizing, powder spreading, granule scattering, and the like.

The herbicides and herbicidal compositions according to the invention can be applied at any stage from pre-emergence and post-emergence.

In the case of the herbicides according to the invention, the amount of the active compound applied can be varied over a wide range depending on the desired effect, but, in general, the amount is about 0.01 kg/ha to about 10 kg/ha, preferably about 0.1 kg/ha to about 2 kg/ha.

Further, in the case of the herbicidal compositions according to the invention, the amount of the composition applied can be varied over a wide range. The amount applied is usually 0.1 kg/ha to 5 kg/ha, preferably 0.2 kg/ha to 3 kg/ha, as the total amount of the effective components.

Compounds according to the invention and their use as herbicides are shown in the following illustrative, non-limiting examples:

Preparation

EXAMPLE 1

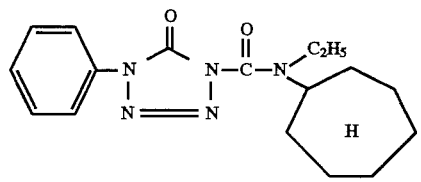

1-Phenyl-5(4H)-tetrazolinone (1.62 g) and 4-dimethylaminopyridine (1.464 g) were suspended in toluene (30 ml) and agitated at room temperature for 10 minutes.

N-cycloheptyl-N-ethylcarbamoyl chloride (2.239 g) was added followed by further agitation at 50° C. for 8 hours. After cooling to room temperature, the precipitated 4-dimethylaminopyridine salt was removed by filtration.

After distilling off the solvent under reduced pressure, the residue was subjected to flash column chromatography (eluent: hexane/ethyl acetate=5:2) to obtain the desired 1-phenyl-4-(N-cycloheptyl-N-ethylcarbamoyl)-5(4H)-tetrazolinone (3.12 g). m.p. 62.5°–64.5° C.

Further compounds of formula (I) obtainable by the above-mentioned reaction procedure are shown in Table 1, together with the compound obtained in the above Example 1.

TABLE 1

| Compound No. | X | Y | R¹ | R² | mp. °C/$n_D^{20}$ |
|---|---|---|---|---|---|
| 1 | H | H | $C_2H_5$ | cycloheptyl | 62.5–64.5 |
| 2 | Cl | H | $C_2H_5$ | cycloheptyl | 1.5467 |
| 3 | Cl | $CH_3$ | $C_2H_5$ | cycloheptyl | 1.5420 |
| 4 | H | H | $CH_3$ | cycloheptyl | 80–82.5 |
| 5 | H | H | $C_3H_7$-n | cycloheptyl | 72–77 |
| 6 | Cl | H | $CH_3$ | cycloheptyl | 82–84 |
| 7 | Cl | H | $C_3H_7$-n | cycloheptyl | 88.5–91.5 |
| 8 | Cl | $CH_3$ | $CH_3$ | cycloheptyl | 1.5500 |

TABLE 1-continued

| Compound No. | X | Y | R¹ | R² | mp. °C/$n_D^{20}$ |
|---|---|---|---|---|---|
| 9 | Cl | $CH_3$ | $C_3H_7$-n | cycloheptyl | 1.5362 |
| 10 | H | H | $C_2H_5$ | cyclooctyl | 1.5478 |
| 11 | Cl | H | $C_2H_5$ | cyclooctyl | 1.5402 |
| 12 | Cl | $CH_3$ | $C_2H_5$ | cyclooctyl | 1.5345 |
| 13 | H | H | $CH_3$ | cyclooctyl | 1.5573 |
| 14 | Cl | H | $CH_3$ | cyclooctyl | 114.5–116.5 |
| 15 | Cl | $CH_3$ | $CH_3$ | cyclooctyl | 69.5–76.5 |

EXAMPLE 2 (Synthesis of starting material)

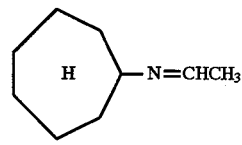

90% Acetaldehyde (19.55 g) was added dropwise to cycloheptylamine (45.28 g) with ice bath cooling over about 2 hours. After the completion of the dropwise addition, potassium hydroxide, in solid form, was added and the organic layer was separated by a separatory funnel. This liquid was distilled under reduced pressure to obtain pure N-ethylidenecycloheptylamine (47.92 g). b.p. 100°–104° C./106.4 mbar.

EXAMPLE 3 (Synthesis of starting material)

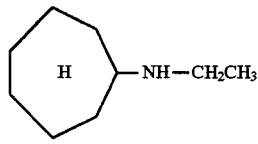

Sodium borohydride (3.78 g) was gradually added with ice bath cooling to a methanol (600 ml) solution of N-ethylidenecycloheptylamine (41.7 g) and agitated at 10° C. for 3 hours. Thereafter, the solvent was distilled off, followed by extraction with methylene chloride. Then, the extract was dried over anhydrous magnesium sulfate. Methylene chloride was distilled off and the obtained oil was distilled under reduced pressure to obtain N-ethylcycloheptylamine (35.96 g). b.p. 110°–113° C./26.6 mbar.

EXAMPLE 4 (Synthesis of starting material)

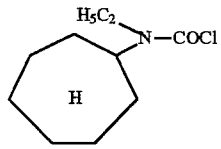

N-ethylcycloheptylamine (21.15 g) was added with ice bath cooling to a mixture consisting of trichloromethylchloroformate (29.7 g) end ethyl acetate (300 ml). Thereafter, the temperature was gradually elevated and heated with refluxing for 6 hours. After distilling off the solvent, the obtained oil was distilled under reduced pressure to obtain N-cycloheptyl -N-ethylcarbamoyl chloride (17.20 g). b.p. 125°–128° C./4.0 mbar.

Biological Test Examples

The following compounds were used as control compounds.

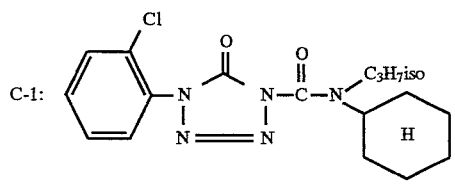

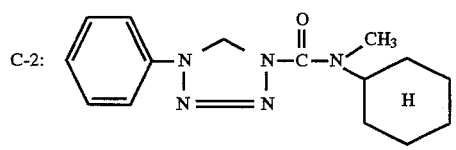

(C-1 and C-2 are compounds disclosed in Japanese Patent Kokai Publication Sho 60-146879.)

EXAMPLE 5 (Biological test)

Herbicidal effect against paddy field weeds
Preparation of formulations
  carrier: acetone, 5 parts by weight
  emulsifier: benzyloxy polyglycol ether 1 part by weight A formulation of active substance is obtained as an emulsion by mixing 1 part by weight of active compound and the above amounts of carrier and emulsifier. A prescribed amount of the formulation is diluted with water to be subjected to the following tests:
Testing method In the greenhouse, for each test, 3 seedlings of paddy rice (cultivar: Nipponbare) of 2.5 leaf stage (15 cm tall) were transplanted in two places in 1/2000 are pot (25×25×9 cm) filled with paddy field soil. Then, seeds of barnyardgrass, smallflower, monochoria, broad-leaved weeds (common falsepimpernel, Indian toothcup, long stemmed water wort, *Ammannia multiflora* Roxb. *Dopatrium junceum* Hammilt) and bulrush were sowed, and water was poured on the soil to a depth of about 2–3 cm. The compositions to be tested were applied to the surface of the water 5 days after transplanting of the paddy rice. The herbicidal effect and the extent of phytotoxicity against crop plants were examined on the 22nd day after the treatment, during which period the water depth of 3 cm was maintained.

The herbicidal effect was rated as 100% in the case of complete death and as 0% in the case where no herbicidal effect was observed. The results are shown in Table 2.

TABLE 2

| compound No. | Rate-concentration (kg/ha) | barnyard grass | smallflower | bulrush | monochoria | broadleaved weeds | phytotoxicity rice |
|---|---|---|---|---|---|---|---|
| 1 | 0.3 | 100 | 100 | 90 | 100 | 100 | 0 |
|   | 0.2 | 90 | 100 | 80 | 95 | 90 | 0 |
| 2 | 0.3 | 100 | 100 | 90 | 100 | 100 | 0 |
|   | 0.2 | 100 | 100 | 80 | 90 | 90 | 0 |
| 4 | 0.3 | 100 | 100 | 90 | 100 | 100 | 5 |
|   | 0.2 | 90 | 100 | 80 | 90 | 90 | 0 |
| 6 | 0.3 | 100 | 100 | 90 | 100 | 100 | 0 |
|   | 0.2 | 100 | 100 | 80 | 90 | 90 | 0 |
| 8 | 0.3 | 100 | 100 | 90 | 100 | 100 | 0 |
|   | 0.2 | 90 | 100 | 70 | 90 | 70 | 0 |
| 10 | 0.3 | 100 | 100 | 80 | 90 | 80 | 0 |
|    | 0.2 | 90 | 100 | 70 | 80 | 60 | 0 |
| 13 | 0.3 | 100 | 100 | 90 | 100 | 90 | 5 |
|    | 0.2 | 90 | 100 | 80 | 90 | 80 | 0 |
| 14 | 0.3 | 100 | 100 | 90 | 90 | 90 | 0 |
|    | 0.2 | 90 | 100 | 80 | 80 | 80 | 0 |
| Comparative |  |  |  |  |  |  |  |
| C-1 | 0.3 | 90 | 100 | 80 | 90 | 60 | 15 |
|     | 0.2 | 80 | 90 | 70 | 80 | 50 | 10 |
| C-2 | 0.3 | 80 | 100 | 70 | 80 | 40 | 15 |
|     | 0.2 | 60 | 80 | 40 | 50 | 30 | 10 |

EXAMPLE 6 (Biological test)

Effect of the herbicidal compositions against paddy field weeds
Method

For each test, 3 seedlings of paddy rice (cultivar: Nipponbare ) of 2.5 leaf stage (15 cm tall) were transplanted in two places in 1/2000 are pot (25×25×9 cm) filled with paddy field soil. Then, seeds of barnyardgrass, smallflower, monochoria, broad-leaved weeds (common falsepimpernel, Indian toothcup, long stemmed water wort, *Ammannia multiflora* Roxb. *Dopatrium junceum* Hammilt) and bulrush and tubers of Japanese ribbon wapato were sowed, and water was poured on the soil to a depth of about 2–3 cm. The mixed active compounds and the active compounds in the form of granules prepared by methods similar to those in Formulation Example 1 were applied to the surface of the water 5 days after transplanting of the paddy rice. The herbicidal effect and the extent of phytotoxicity against crop plants were examined and rated as %, on the 22nd day after the herbicidal treatment, during which period the water depth of 3 cm was maintained.

100%: complete death

0%: no effect was observed, or no phytotoxicity was observed.

The results are shown in Table 3.

In the table, A and B in the column of applied compound represent the following active compounds:

A: methyl 2-[3-(4,6-dimethoxypyrimidin-2-yl) ureidosulfonyl-methyl]benzoate

B: ethyl 5-[3-(4,6-dimethoxypyrimidin-2-yl)ureidosulfonyl]-1-methylpyrazol-4-carboxylate

TABLE 3

| applied compound | amount of effective component kg/ha | herbicidal effect % | | | | | | phytotoxicity % rice |
|---|---|---|---|---|---|---|---|---|
| | | barnyard grass | smallflower | monochoria | broadleaved weeds | bulrush | Japanese ribbon wapato | |
| 1 + A | 0.125 + 0.075 | 100 | 100 | 100 | 100 | 100 | 100 | 0 |
| 2 + A | 0.125 + 0.075 | 100 | 100 | 100 | 100 | 100 | 100 | 0 |
| 4 + A | 0.125 + 0.075 | 100 | 100 | 100 | 100 | 100 | 100 | 0 |
| 2 + B | 0.125 + 0.021 | 100 | 100 | 100 | 100 | 100 | 100 | 0 |
| 13 + B | 0.125 + 0.021 | 100 | 100 | 100 | 100 | 100 | 100 | 0 |
| 1 | 0.125 | 80 | 100 | 80 | 80 | 60 | 0 | 0 |
| 2 | 0.125 | 80 | 100 | 80 | 70 | 60 | 0 | 0 |
| 4 | 0.125 | 70 | 100 | 70 | 70 | 50 | 0 | 0 |
| 13 | 0.125 | 70 | 100 | 80 | 80 | 60 | 0 | 0 |
| A | 0.075 | 40 | 100 | 100 | 100 | 100 | 100 | 0 |
| B | 0.021 | 50 | 100 | 100 | 100 | 100 | 100 | 0 |

FORMULATION EXAMPLE 1 (granules)

Water is added to a mixture of Compound No. 1 (1 part by weight), active compound A (0.25 parts by weight), bentonite (30 parts by weight), talc (66.75 parts by weight) and lignin sulfonate salt (2 parts by weight) with kneading, followed by granulation-drying to give granules.

It will be understood that the specification and examples are illustrative but not limitative of the present invention and that other embodiments within the spirit and scope of the invention will suggest themselves to those skilled in the art.

We claim:

1. A tetrazolinone of the formula:

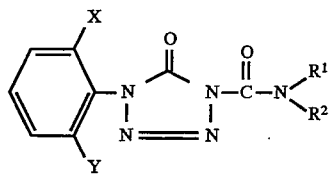

(I)

wherein

X is hydrogen or halogen,

Y is hydrogen or $C_{1-4}$ alkyl, $R^1$ is $C_{1-4}$ alkyl, and $R^2$ is cycloheptyl or cyclooctyl.

2. A compound according to claim 1, wherein

X is chlorine,

Y is hydrogen or methyl, $R^1$ is ethyl or n-propyl, and $R^2$ is cycloheptyl or cyclooctyl.

3. A compound according to claim 1, wherein such compound is 1-phenyl-4-(N-cycloheptyl-N-ethyl-carbamoyl)-5(4H)-tetrazolinone of the formula

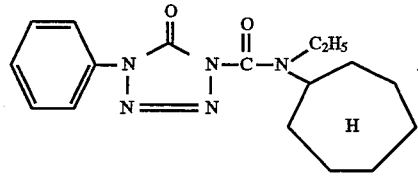

(1)

4. A compound according to claim 1, wherein such compound is 1-(2-chlorophenyl)-4-(N-cycloheptyl-N-ethyl-carbamoyl)-5(4H)-tetrazolinone of the formula:

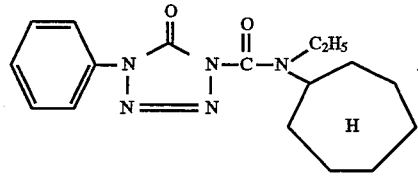

(2)

5. A compound according to claim 1, wherein such compound is 1-(2-chloro-6-methylphenyl)-4-(N-cycloheptyl-N-ethyl-carbamoyl)-5(4H)-tetrazolinone represented by the formula

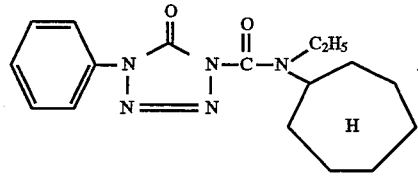

(3)

6. A compound according to claim 1, wherein such compound is 1-phenyl-4-(N-cycloheptyl-N-methyl-carbamoyl)-5(4H)-tetrazolinone of the formula

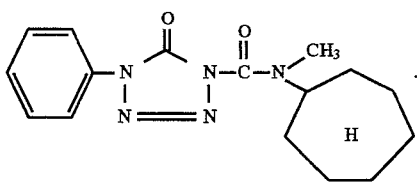

(4)

7. A compound according to claim 1, wherein such compound is 1-phenyl-4-(N-cyclooctyl-N-methyl-carbamoyl)-5(4H)-tetrazolinone of the formula

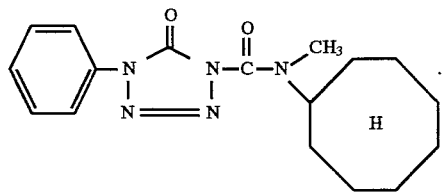

8. A herbicidal composition comprising a herbicidally effective amount of a compound according to claim 1 and a diluent.

9. A method of combatting unwanted vegetation which comprises applying to such vegetation or to a locus from which it is desired to exclude such vegetation a herbicidally effective amount of a compound according to claim 1 and a diluent.

10. The method according to claim 9, wherein the compound is applied to a paddy field in which a crop is growing or is to grown and is selected from the group consisting of 1-phenyl-4-(N-cycloheptyl-N-ethyl-carbamoyl)-5(4H)-tetrazolinone, 1-(2-chloro-6-methylphenyl)-4-(N-cycloheptyl-N-ethyl-carbamoyl)-5(4H)-tetrazolinone, 1-phenyl-4-(N-cycloheptyl-N-ethyl-carbamoyl)-5(4H)-tetrazolinone, and 1-phenyl-4-(N-cyclooctyl-N-methyl-carbamoyl)-5(4H)-tetrazolinone.

\* \* \* \* \*

UNITED STATES PATENT AND TRADEMARK OFFICE
CERTIFICATE OF CORRECTION

PATENT NO.   : 5,652,198
DATED        : July 29, 1997
INVENTOR(S)  : Goto, et al.

It is certified that error appears in the above-indentified patent and that said Letters Patent is hereby corrected as shown below:

Title Page   [30] Foreign Application Priority Data:
             Delete " Mar. 10, 1995 " and substitute
             Mar. 13, 1995 --

Signed and Sealed this

Second Day of June, 1998

Attest:

BRUCE LEHMAN

Attesting Officer          Commissioner of Patents and Trademarks